United States Patent [19]

McClellan

[11] Patent Number: 5,540,239
[45] Date of Patent: Jul. 30, 1996

[54] CHILD RESTRAINT

[76] Inventor: Nancy McClellan, 1036 E. 820 North, Provo, Utah 84601

[21] Appl. No.: 401,716

[22] Filed: Mar. 10, 1995

[51] Int. Cl.[6] .............................. A61B 19/00; A61F 5/37
[52] U.S. Cl. .......................................... 128/869; 128/876
[58] Field of Search .................................... 128/846, 845, 128/869–876; 602/19; 2/49.3, 46, 48, 310; 269/485, 484, 465, DIG. 6

[56] References Cited

U.S. PATENT DOCUMENTS

| | | | |
|---|---|---|---|
| D. 290,765 | 7/1987 | Callahan | D29/11 |
| 1,332,328 | 3/1920 | Fisher . | |
| 1,930,378 | 10/1933 | Beagen | 128/875 |
| 2,413,395 | 12/1946 | Ware | 227/49 |
| 2,851,033 | 9/1958 | Posey | 128/134 |
| 3,062,585 | 11/1962 | Bentley | 297/484 |
| 3,191,599 | 6/1965 | Kendell | 128/134 |
| 3,276,432 | 10/1966 | Murcott | 128/874 |
| 3,604,750 | 9/1971 | Doering | 297/484 |
| 3,612,605 | 10/1971 | Posey | 297/389 |
| 4,205,670 | 6/1980 | Owens | 128/875 |
| 4,226,474 | 10/1980 | Rupert et al. | 297/484 |
| 4,312,334 | 1/1982 | Munoz | 602/19 |
| 4,667,624 | 5/1987 | Smith | 119/96 |
| 4,834,460 | 5/1989 | Herwig | 297/485 |
| 4,927,211 | 5/1990 | Bolcerek | 297/465 |
| 5,002,338 | 3/1991 | Gisser | 297/250 |
| 5,069,168 | 12/1991 | Roberson et al. | 119/96 |
| 5,106,152 | 4/1992 | Ward | 297/DIG. 6 |

Primary Examiner—Michael A. Brown
Attorney, Agent, or Firm—Berne S. Broadbent; A. John Pate; Gary D. E. Pierce

[57] ABSTRACT

An apparatus for restraining a child or adult in a chair, shopping cart, high chair, stroller, carriage, wheelchair, or the like, has a plurality of straps adapted to cross the body of the restrained person. A fastener is attached to the free end of each strap. Each fastener is attachable to members of the chair. Fasteners may be made adjustable, or a separate adjuster may be included on the strap. The apparatus may be made with three, four or five straps to restrain the waist, chest, head and legs of a seated person against movement away from a seatback more than a selected distance.

20 Claims, 7 Drawing Sheets

CHILD RESTRAINT

BACKGROUND

1. The Field of the Invention

This invention relates to apparatus for restraining children and, more particularly, to novel systems and methods for safely restraining children to a seat in a carriage, stroller, chair, shopping cart or the like.

2. The Background Art

Children are active, growing, agile, curious, and resourceful. The propensity of children to move about, climb, squirm, explore, and wander is well known. Parents and guardians of children must be vigilant in protecting small children from wandering away, climbing out of shopping carts, falling from chairs, pitching forward out of strollers, and similar dangers. Even while a child is being fed, a momentary distraction of a parent may give opportunity to the child to squirm out of a chair in any convenient direction. Very small children can retract an arm or leg from a belt or strap very easily in many instances. Toddlers may lean, stand, slide or otherwise squirm out of a chair, even a high chair having a safety belt. Children may move so quickly that they represent a large risk, even for an attending adult who steps away momentarily to answer a telephone or retrieve food from a refrigerator across a room.

Also, sitters, grandparents, relatives and a host of others have occasional responsibility for small children. Many times these people are not equipped to regularly attend to the specific needs of the children. For example, a high chair for feeding a child may not be available. Perhaps a high chair is available, but three visiting children must be fed. A child restraint that can easily adapt any chair to serve as a high chair is needed. Also, a restraint that is comfortable, easily operated, and not easily defeated is needed for chairs and high chairs alike, as well as for shopping carts and carriages.

In addition, older infirm persons may need assistance in remaining upright in a chair. A safe restraint is needed to comfortably secure such a person in a chair. Adequate breathing requires a healthy posture for many guests at nursing homes. An attendant cannot stand all day in a sun room with each guest. Restraining a guest with makeshift straps may be cause for great liability. A simple, effective, economical restraint is needed for adults A simple, safe, reliable restraint is not available for these applications. Particularly, an economical, washable, portable restraint that is adaptable to a carriage, stroller, chair and shopping cart is not available.

Restraints that are available are typically of two types. The first type is a body harness that resembles a parachute harness. These harnesses typically fit the body closely and uncomfortably. The harness must be provided with clips, fasteners, ties and the like for fastening to specialized anchors on a chair or at another location. Anchoring the harness at enough points to restrict motion in three dimensions is difficult. If successful, anchoring the harness in three dimensions is bulky and uncomfortable. Such a system will typically involve pounds of hardware or many feet of cumbersome strapping.

The second type of restraint is a system of straps that buckle, tie, wrap, and otherwise bundle a person and chair into a monolith. Typically, these restraints wrap around a seated person, fastening together two ends of a strap behind the chair, or under the chair. Several straps may be used. Two or more hands are needed to reach the two ends of each strap, bring them together and fasten them. A seated patient or child cannot be held while the restraint is being placed and fastened. Moreover, this type of restraint cannot typically be attached comfortably to a small child in a full-sized chair. The straps must pass completely around the chair, which defines the length of the straps. The envelope of the restraint includes the entire chairback, an object much larger than a small child. The result is that a restraint may be either uncomfortably tight, or else a child can tip to one side or another. In fact, a child can fall completely out of a chair and still be within the envelope circumscribed by the restraint. If such a restraint is loosened enough to be comfortable, a child could conceivably move to one side and become caught between the straps of the restraint and the edge of the chairback.

The systems available tend to be bulky, heavy, difficult to fit, not highly adjustable or else often tangled. Simpler systems are easily defeated. Children are especially adept at escaping from belts and tethers in all their varieties.

Infirm patients may be put at great risk after becoming improperly positioned in inadequate or makeshift restraints. Restraints may carry labels warning that patients and children should not be left unattended. The reality is that attention will never be uninterrupted, and a restraint must be reliable.

An inexpensive, reliable, safe restraint for children is not readily available. A strong, light, small, portable restraint is not available. A restraint that could fit in a diaper bag, taking no more space than a baby bottle or a diaper is needed. An economical restraint that can be readily washed for re-use should be available to a grandparent tending visiting children. Day care centers, hospitals, and nursing homes should be able to economically provide a restraint for any guest who requires it at any time. The restraints should be easily washable when soiled. A strong, compact, washable, adjustable, effective, inexpensive restraint is needed.

BRIEF SUMMARY AND OBJECTS OF THE INVENTION

In view of the foregoing, it is one object of the present invention to provide a restraint for children seated in chairs, carriages, shopping carts, high chairs, and the like.

Another object of the invention is to reduce the weight and size of the restraint.

It is an object to provide, for restraint of small children, a compact, portable restraint that can be carried easily in a purse or diaper bag for use by a sitter, grandparent or parent.

One object is to provide safe restraint with a comfortable degree of motion available to a restrained child or adult.

It is an object to provide a restraint that is easily washable.

It is an object of the invention to provide an adjustable restraint readily adaptable to a variety of sizes of persons to be restrained.

Another object is to provide a restraint that can be completely adjusted with a single hand.

One object of the invention is to provide a restraint that can be attached with a single hand, leaving the other hand free to hold the child being restrained.

Another object of the invention is to provide a restraint for eliminating access to the edge or back side of the chair by a restrained person, even with the restraint in a very loose position.

Another object of the invention is to provide a restraint that restricts a person to the front side of a chairback.

Another object of the invention is to provide a restraint that connects directly to a chair or the like, rather than to itself.

Another object of the invention is to connect an end of each strap directly to the chair rather than to itself or to the other end of itself another strap.

Another object of the invention is to provide a connection mechanism that permits each strap to be optionally connected to another strap, or to the chair directly, to assure compatability with a broad variety of chair types, and chair back configurations.

Another object is to provide for fastening each strap to any of the nearest members of a chair having the smallest, structurally sound, dimension.

Yet another object is to provide a restraint that can be easily untangled even if carelessly or improperly stored.

Features of an apparatus for restraining a person include restricting movement to a front side of a seatback. A person may be seated on a seat associated with the seatback. A waist strap has a first end and a second end, and extends across the front of the waist of the person. The first end and the second end extend to the seatback. A chest strap may be spaced upwardly away from the waist strap, to extend across the front of the chest and under the arms of the person.

The chest strap includes a left end and a right end, each extending to the seatback. A left shoulder strap connects to the waist strap and the chest strap, extending over one shoulder of the person and terminating at a first free end. A right shoulder strap may be connected to the waist strap and the chest strap, extending over another shoulder of the person and terminating at a second free end.

A first fastener may be attached to the first end for fastening the first end to one of the members, such as an elongate member of the seatback. In similar fashion a second fastener attaches to the second end for fastening the second end to another elongate member of the seatback. Corresponding fasteners individually connect the left end, right end, first free end, and second free end to the seatback in similar fashion.

A strap in an embodiment constructed according to a contemplated best mode for practicing the invention may be, for example, a thin, elongate member having a length at least an order of magnitude or larger than a width thereof, and a thickness an order of magnitude less than the width. A strap may include certain types of belts, webbing, fabric strips and the like.

The apparatus may be constructed without a chest strap, and may have any of the foregoing straps with or without a lap strap extending from the waist strap, between the legs of a person to connect by a fastener to a locations such as, for example, the lower end of the seatback, or even around an entire seatback lacking other apertures. Since a belt-like webbing may be contemplated for the straps, the lap strap will lie flat on the seat and may be twisted to wrap around the narrow aspect of an elongate member of the seatback.

Each strap may be provided with an adjuster having a control for selectively taking up and releasing a length of the strap. Each control may be operable by a single hand of an operator, as may each fastener. Thus, an operator may restrain or support a person with one hand, while attaching each fastener and adjusting each strap one at a time with a free hand.

Advantages of an apparatus constructed consistent with the invention include light weight, simplicity, washability, adjustability, and adaptability to many styles of seats, including ladder-back chairs, slat-back chairs, shopping carts, and the like.

A chair may be any means for seating a person. A chairback or seatback, may include, for example, any support against which the back of a user may rest. The seatback may be an associated part of a chair, a stroller, a shopping cart, a wheelchair, a high chair or the like. A seat may include any surface or object that supports a substantial portion of a person's weight when seated.

The apparatus may be tangle-proof. When not fastened to a seatback, the apparatus may be attached one member at a time, each with a single hand. An operator need not hold more than one strap at a time. The entire apparatus can be laid flat, with no complex wrapping, assembly, displacement, or attachment of straps or fasteners. A minimum number of hardware pieces may be required, reducing bulk, weight, cost, and complexity. The length of the straps may be less than other harnesses for restraining seated children and adults, largely because no strap has to wrap around the entire width of the seatback nor around the entire person seated. The apparatus may be easily portable in a compact bundle.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
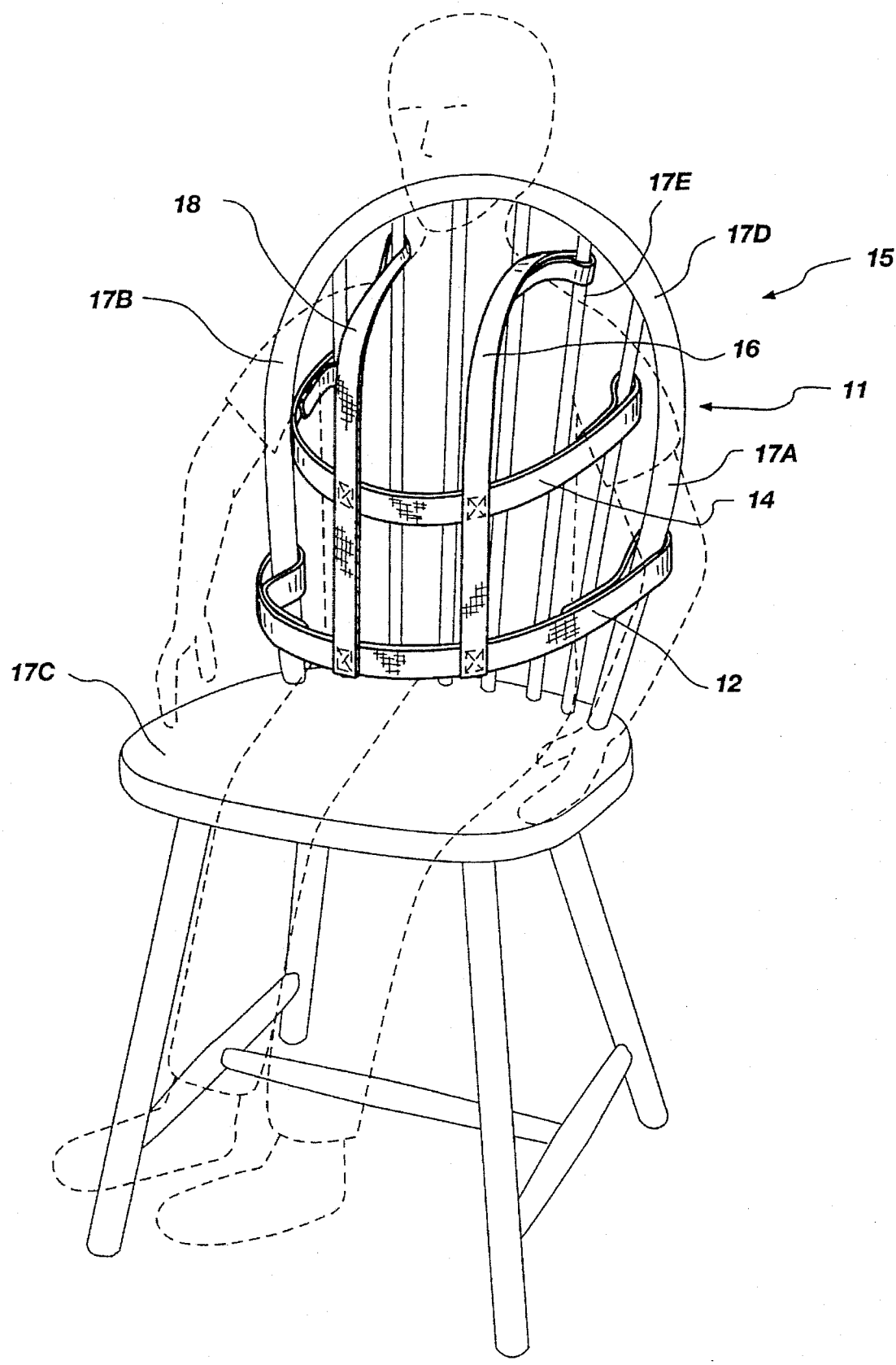
FIG. 1 is a frontal isometric view of an apparatus made in accordance with the invention.

It will be readily understood that the components of the present invention, as generally described and illustrated in the figures herein, could be arranged and designed in a wide variety of different configurations. Thus, the following more detailed description of the embodiments of the system and method of the present invention, as represented in FIGS. 1 through 8, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

The apparatus is best understood by reference to FIGS. 1–8. A restraint 10 (apparatus 10), for restraining a person seated against a seatback 11 may include a waist strap 12 for extending across the front of the waist of the person. The waist strap 12 may attach to any of a plurality of members 13 of the seatback 11. Each of the members 13 may be elongate in shape, and may be configured in any orientation and location on a seatback 11.

For example, the seatback 11 of a chair 15 of the slat-back type typically has side posts 17A, 17B extending upward from the seat 17C to a top bar 17D. The side posts 17A, 17B and top bar 17D may be a single bowed piece. Slats 17E extend between the top bar 17D and either a similar bottom bar 17F or the seat 17C. Slats 17E may have a rectangular, circular, or other cross-section.

By contrast, the seatback 11 of a chair (FIGS. 7–8) 15 of the ladder-back type has slats 17E passing horizontally between the two side posts 17A, 17B. Any convenient member 13 of the seatback 11 may be used as a member 13 for attachment of the waist strap 12 or similar structures of the restraint 10 (apparatus 10). The term "members" 13 thus applies to at least all the foregoing structures 17A, 17B, 17D, 17E, 17F.

Attachment to an elongate member 13 may be determined primarily by proximity and convenience. Wherever a strap 12, 14, 16, 18, 20 conveniently extends, it may be attached to a member 13 of a chair 15.

A chest strap 14 may be spaced apart from and above the waist strap 12 for extending across the front of the chest and under the arms of the seated person. Shoulder straps 16, 18 may attach to the waist strap 12 and chest strap 14, extending over the left and right shoulders, respectively, of the person.

A lap strap 20 may be connected to the waist strap 12, shoulder straps 16, 18, or all of them. The lap strap 20 may extend between the legs of the person toward the seatback 11 to be attached to a convenient member 13.

The straps 12, 14, 16, 18, 20 (see FIGS. 2–6) may be connected to one another at joints 22. Each strap 12, 14, 16, 18, 20 may be provided with an adjuster 24, (see FIG. 5) and may have one or more fasteners 26 for connecting to members 13 of the seatback 11.

The waist strap 12 may include a base 30 formed of webbing, fabric, or other material that is flexible in a transverse direction 31. The base 30 may be inextensible, but may stretch elastically under forces larger than the person would ordinarily exert.

Figure 2:
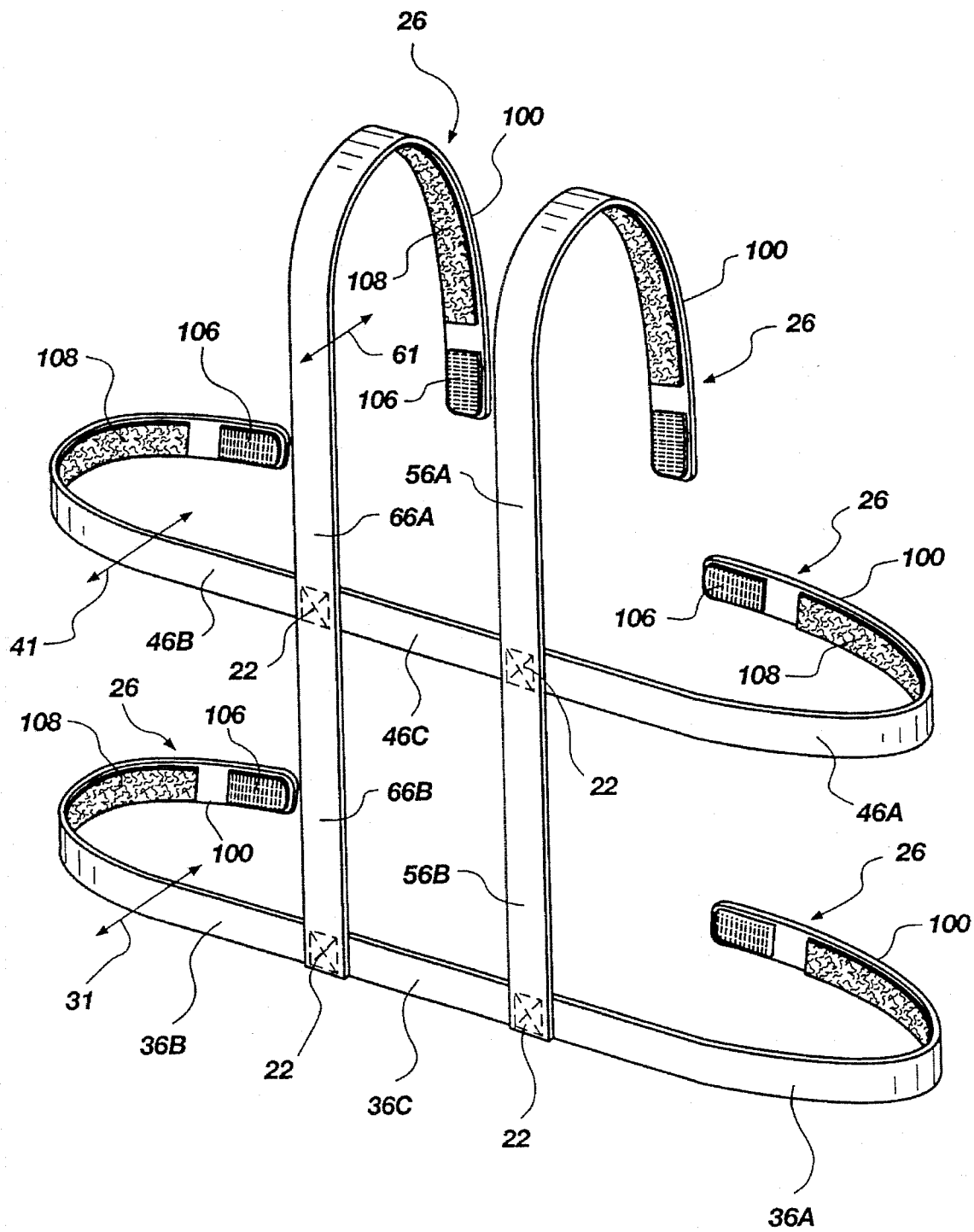
FIG. 2 is an isometric view of the apparatus of FIG. 1.
Figure 3:
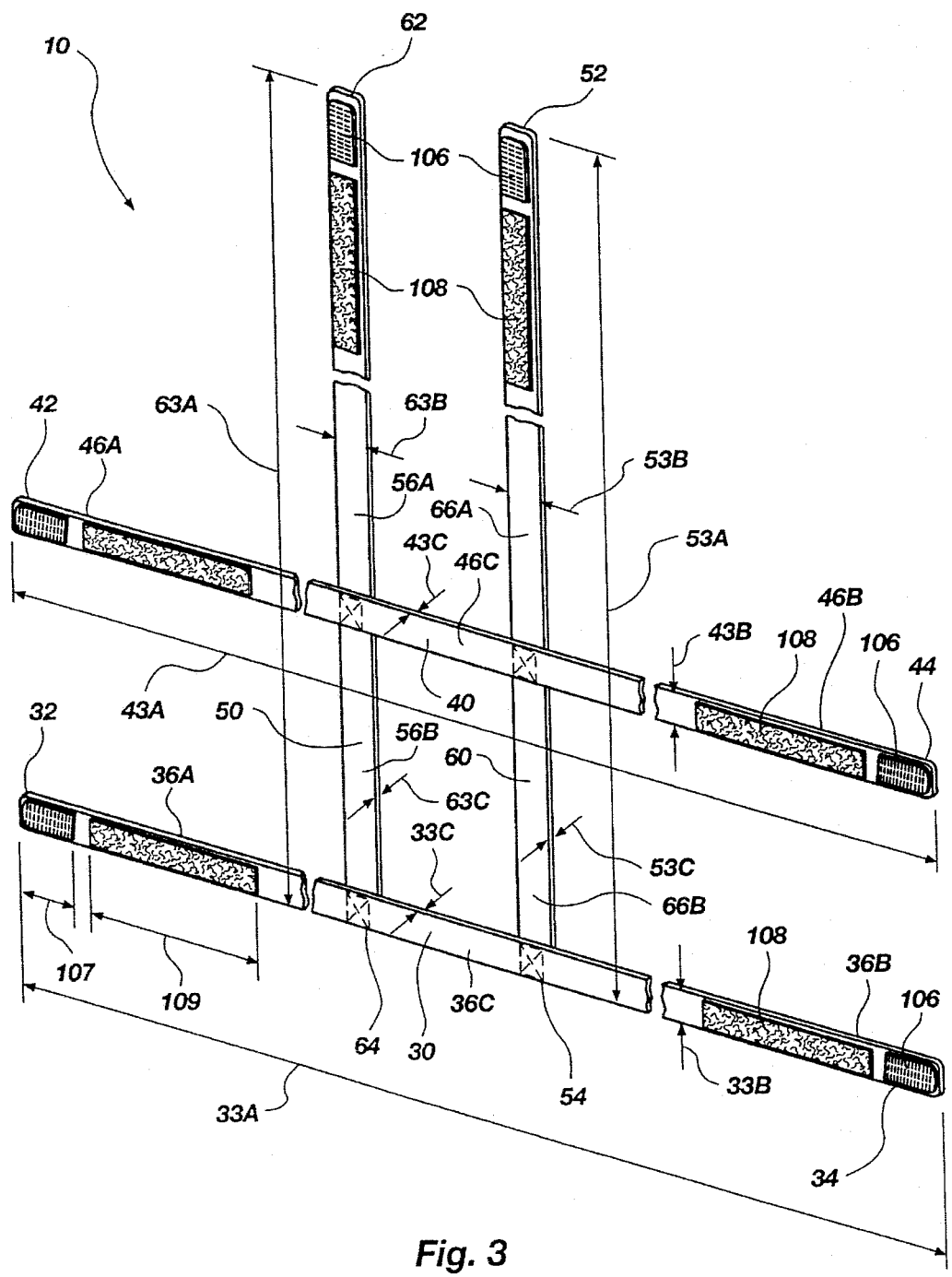
FIG. 3 is a rear isometric view of the apparatus of FIG. 1, laid flat.
Figure 4:
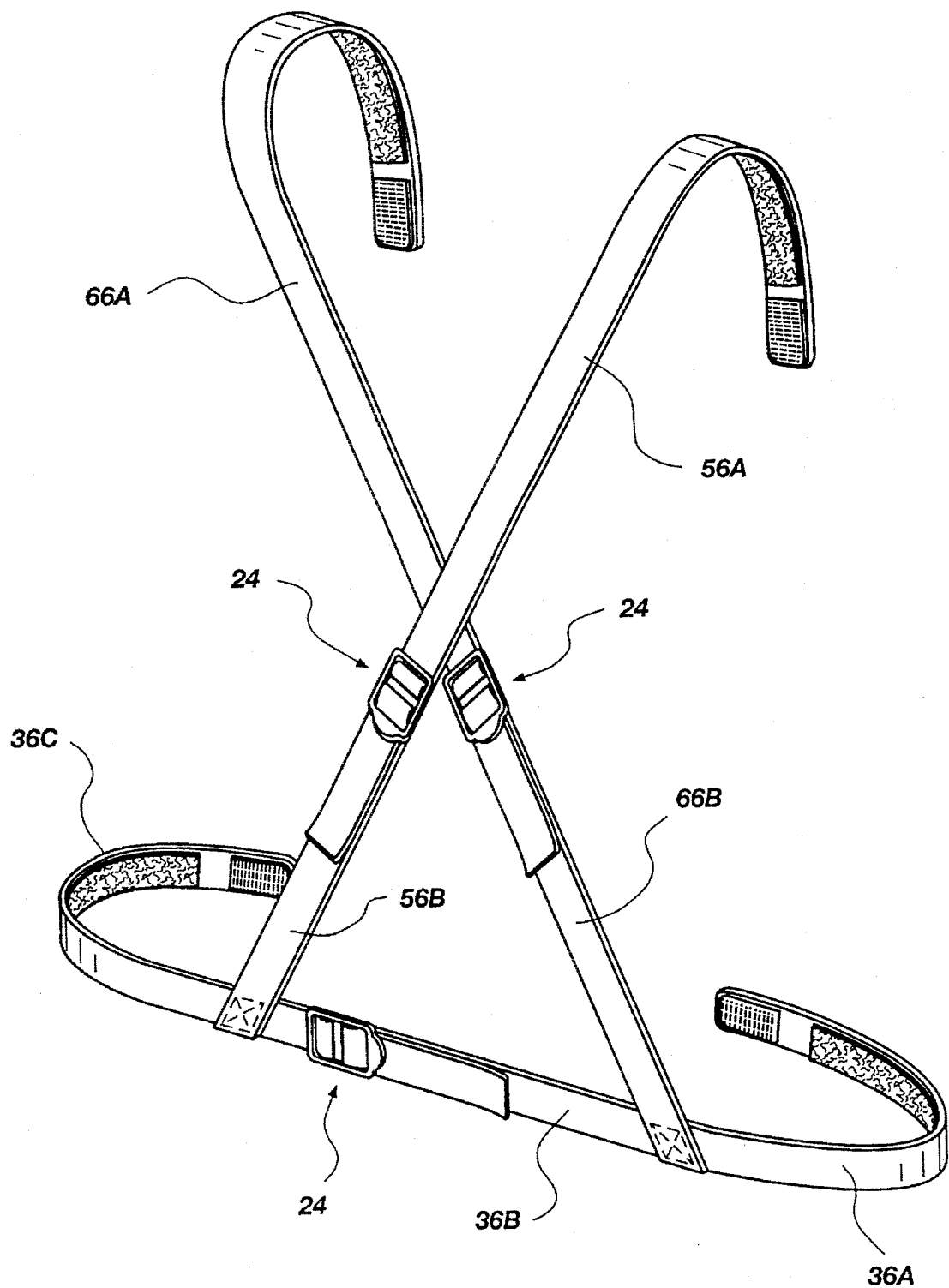
FIG. 4 is an isometric view of an alternate embodiment of the apparatus of FIG. 1.

Referring to FIGS. 1–3, the waist strap 12 may extend from an end 32 to an end 34. The length 33A of the base 30 may extend from a member 13 of the seatback 11, around the seated person, and back to a different member 13 of the seatback. The width 33B may be selected to restrain the person without exerting undue pressure against the person. The thickness 33C of the base 30 may be selected to provide structural integrity and dimensional stability to the base 30. Thus, the width 33B and thickness 33C may vary with the material chosen for the base 30.

The base may include the spans 36A, 36B, with the span 36C therebetween. The base 30 may be continuous between the ends 32, 34. However, the spans 36A, 36B, 36C may be continuous or discontinuous within themselves and with respect to one another in various embodiments. For example, adjusters 24 and fasteners 26 may be interposed along the base 30 at appropriate locations to alter the effective length 33A.

Similarly, the chest strap 14 includes a base 40, and may be of the same material as the base 30. The base 40 may be made of a material that is flexible in the transverse direction 41. The base 30 may be fabricated satisfactorily from a material such as nylon, polyethylene, polypropylene or other olefinic fiber, cotton, rayon, acrylic or the like, woven into a durable webbing, duck or similar weave.

The base 40 of the chest strap 14 extends from the end 42 a length 43A to the end 44. The base 40 comprises the spans 46A, 46B, 46C. The width 43B and thickness 43C may be constant along the entire length 43A, and may be selected to be comparable or identical to the width 33B and thickness 33C, respectively. Likewise the sizes and materials for the base 40 may be similar or identical to those of the base 30.

The base 50 of the shoulder strap 16 extends from the end 52 along the length 53A to the end 54. The material as well as the width 53B and thickness 53C of the shoulder strap 16 may be selected to be compatible with, similar to, or identical to those of the waist strap 12, chest strap 14, or both. The spans 56A, 56B, 56C make up the base 50, and may be continuous or discontinuous. Adjusters 24 may be interposed at discontinuities in the base 50.

A shoulder strap 18 may be similar to or an identical mirror image of the shoulder strap 16. A base 60 extends from the end 62 along the length 63A to the end 64. The width 63B and thickness 63C may be equivalent to the width 53B and thickness 53C, respectively, and for the same reasons. The spans 66A, 66B and 66C make up the base 60 and may be continuous or discontinuous. Adjusters 24 may be interposed at discontinuities in the base 60.

Figure 5:
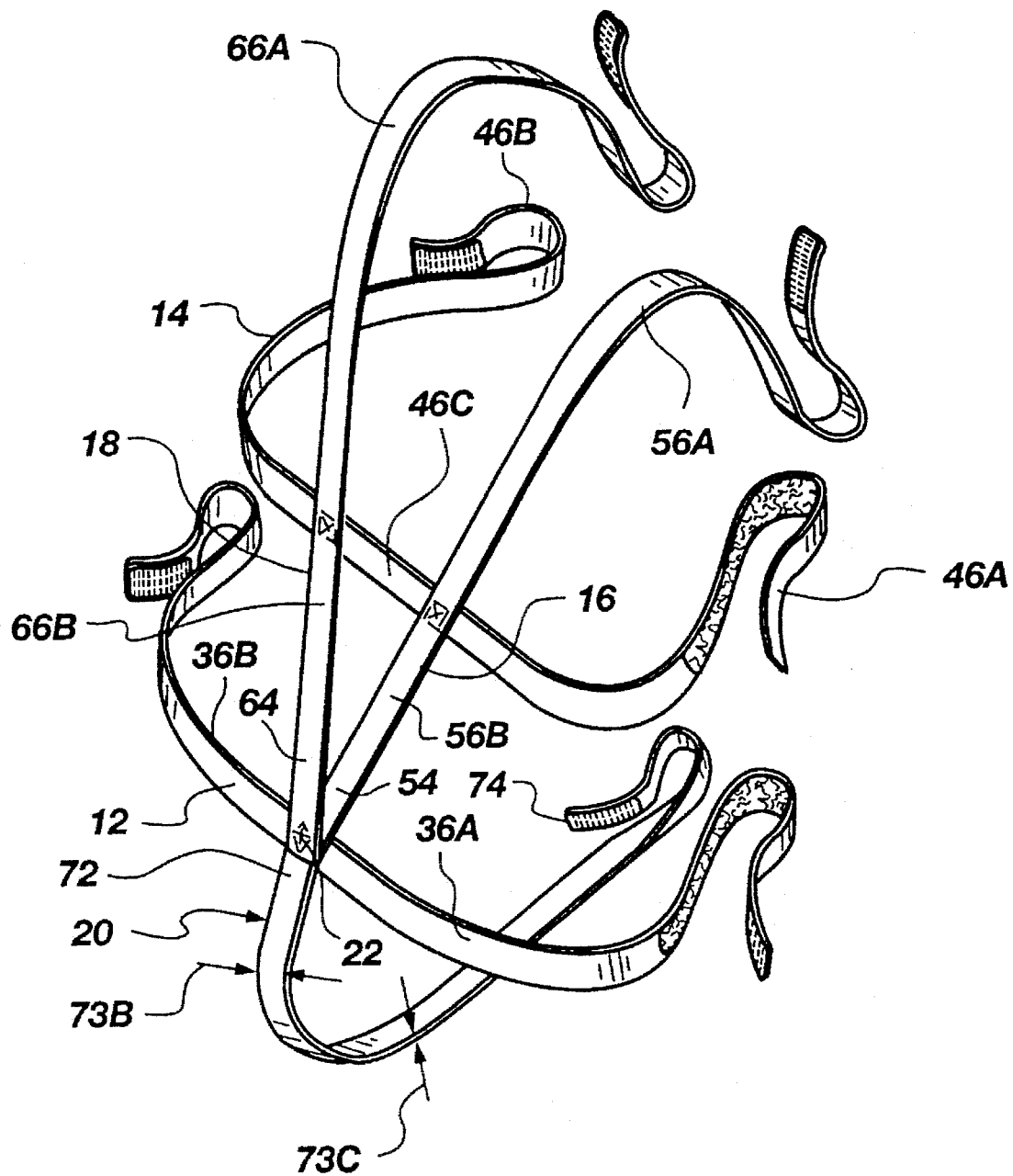
FIG. 5 is an isometric view of an alternate embodiment of the apparatus of FIG. 1.

The shoulder straps 16, 18 may be arranged parallel to one another as in FIGS. 1–3. Alternatively, the shoulder straps 16, 18 may be crossed above the waist strap 12 (FIG. 4) or at the waist strap 12 (FIG. 5). All illustrated embodiments of the restraint 10 may have an optional chest strap 14, or have none at all.

Referring to FIG. 5, a lap strap 20 may be attached to the waist strap 12. The lap strap 20 may extend from an end 72 connected at the joint 22 to the end 74 at the seatback 11. The lap strap 20 may lie flat on the seat 17C, yet twist to fasten around a member 13 of the seatback 11. The lap strap 20 may be joined near one end 72 to the waist strap 12. In the embodiment of FIG. 5, the shoulder straps 16, 18, and lap strap 20 may be all attached near the ends 54, 64, 72, respectively, to the waist strap 12 at a single joint 22.

Figure 6:
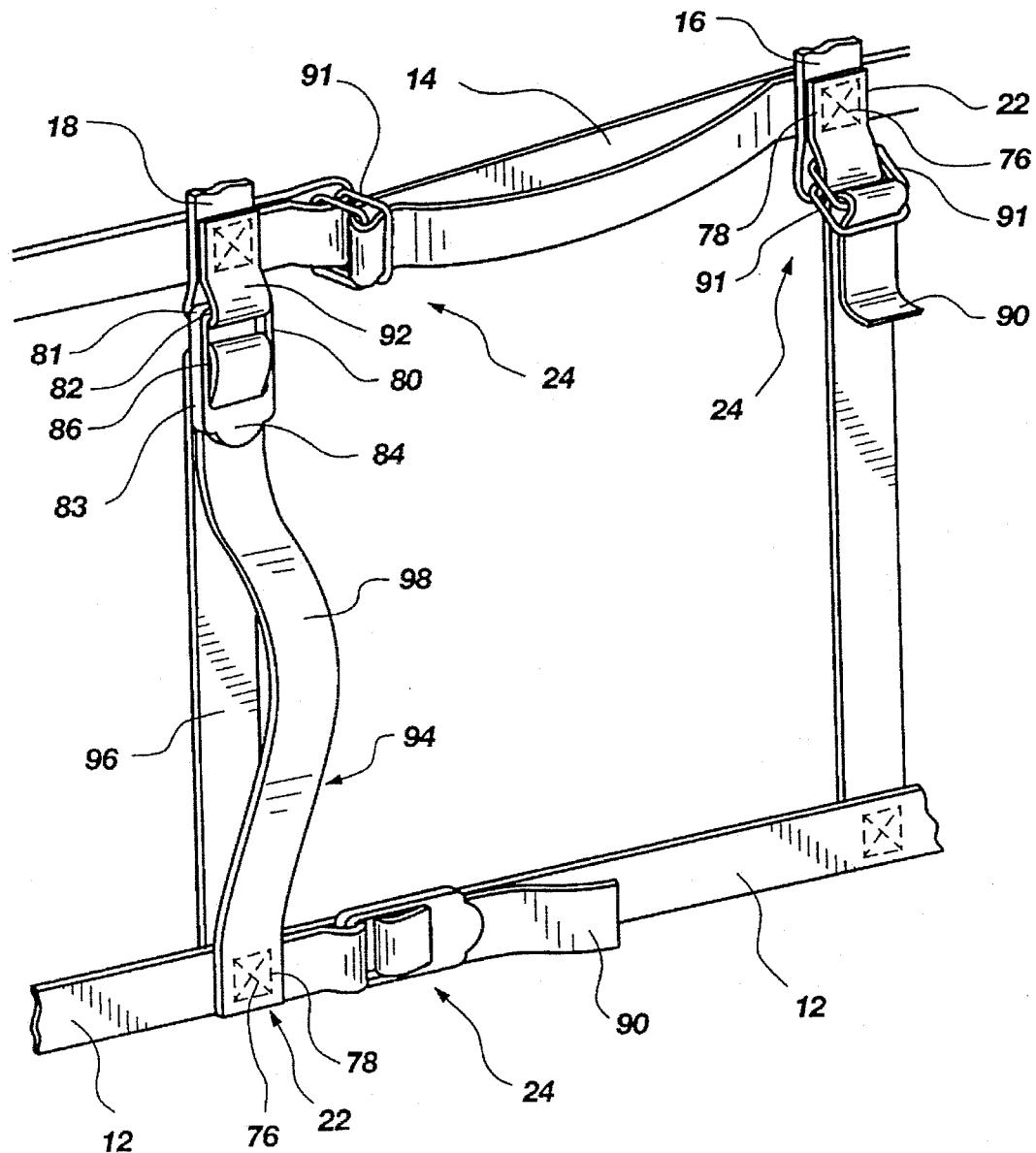
FIG. 6 is an isometric view of alternative embodiments of adjusters for the straps of the apparatus of FIG. 1.
Figure 7:
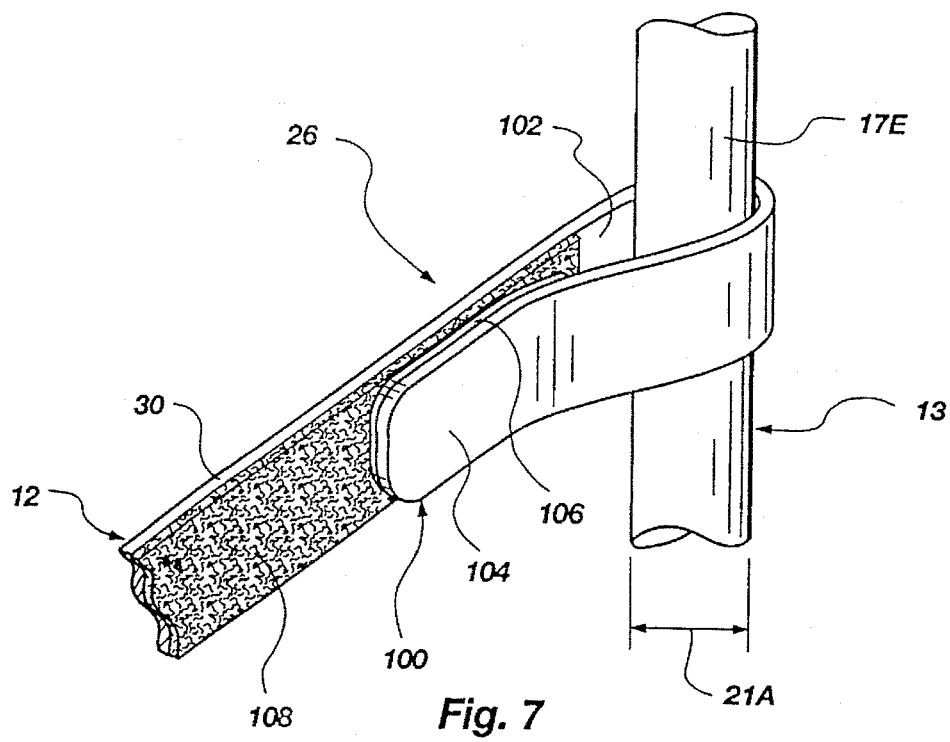
FIGS. 7–8 are isometric views of alternate embodiments of fasteners on the apparatus of FIG. 1.

Referring to FIG. 6, the joint 22 may be fastened permanently by a fastener such as a rivet, seam, staple or equivalent fastener. In the illustrated embodiments, cross seams 76 extend across the joint 22, and edge seams 78 close the joint 22. A strong, durable material may be selected from available threads for sewing the seams 76, 78.

As illustrated in FIG. 6, adjusters 24 may be connected at any position along the strap 12, 14, 16, 18, 20 for adjusting the respective length 33A, 43A, 53A, 63A, 73A. The adjusters 24 may include a bracket 80. Many types of brackets 80 may be commercially available. The adjuster 24 may be positioned anywhere, but may render a respective strap 12, 14, 16, 18, 20, discontinuous. A bracket 80 may be typically designed to join two pieces of material, one of which passes through the bracket 80 a selected distance.

One bracket 80 may include a pivot bar 82 near an end 81, and a tab 84 near the other end 83. The pivot bar 82 may rotate freely within a loop 92 formed in a strap 12, 14, 16, 18, 20. The tab 84 may be configured for lifting by an operator, thus rotating the bracket 80 around the pivot bar 82. A wrap bar 86 may be spaced away from the tab 84 sufficiently to pass a strap 12, 14, 16, 18, 20 therearound.

A free end 90 may be passed from behind the wrap bar 86, between the pivot bar 80 and the wrap bar 86, over the wrap bar 86, and back through between the tab 84 and the wrap bar 86. Alternatively a free end 90 may pass over 'D'-rings 91.

An operator may pull on a free end 90 to draw on a strap 12, 14, 16, 18, 20. As illustrated, a free end 90 may be used to shorten the shoulder strap 16. Another free end 90 may be used to shorten the chest strap 14. The 'D'-rings usually require two hands to release the free end 90 to lengthen a strap 12, 14, 16, 18, 20. By contrast, the tab 84 on a bracket 80 permits single handed operation. Lifting the tab 84 permits the free end 90 to slide freely between the lock bar 88 and the wrap bar 86. In the illustrated embodiment of FIG. 6, a free end 90 may be held against the tab 84 by tension in the strap 12, 14, 16, 18, 20.

To eliminate escape of a free end 90 from a bracket 80, or "D" rings 91, a loop 94 may be formed in a strap 12, 14, 16, 18, 20. The loops 94 may be formed in the shoulder strap 18 and waist strap 12. Each loop 94 may be threaded through a bracket 80 or "D" rings 91. The loop 94 may be threaded through the bracket 80 between the pivot bar and the wrap bar 86, wrapped around the wrap bar 86 and passed between the wrap bar 86 and the tab 84. The loops 94 may then form a loaded portion 96 and a slack portion 98 for each of the straps 12, 14, 16, 18, 20, in which formed. By grasping the slack portion 98, an operator may shorten the loaded portion 96 of the loop. Thus, to shorten any strap 12, 14, 16, 18, 20 to which a loop may be attached or integral, one need only pull on the slack portion 98. To release the bracket 80, lengthening out the strap 12, 14, 16, 18 equipped with an adjuster 24, one need only release the 'D' rings, or lift the tab 84 away from the loaded portion 96 of any loop 94.

The loops 94 have the advantage that they prevent any loose end 90 from escaping through a bracket 80. Upon release by the bracket 80 or the "D" ring 91, the loop 94 returns to a balanced loading condition with the loaded portion 96 and slack portion 98 extending substantially equally.

Moreover, since no loose ends 90 exist with the loop 94, the entire restraint 10 can be completely adjusted with no separation or tangling of straps 12, 14, 16, 18. 20. Each embodiment of the bracket 80 and all equivalents may be equally applicable to the embodiments of FIG. 6.

Referring to FIGS. 1–4 AND 6–7, fasteners 26 may be connected near each end 32, 34 of the waist strap 12; ends 42, 44 of the chest strap 14; ends 52, 62 of the shoulder straps 16, 18, respectively; and the end 74 of the lap strap 20. As illustrated in FIGS. 2–3 and 7–8, fasteners 26 may be formed on a tongue 100 near the end 32, 34, 42, 44, 52, 62, 74 of each strap 12, 14, 16, 18, 20, respectively. A hook-and-loop material may be disposed on an inside surface 102 or outside surface 104 of the tongue 100.

For example, a hook panel 106 may be attached nearest the end, 32, 34, 42, 44, 52, 62, 74. The hook panel 106 may extend along the tongue 100 a length 107. A loop panel 108 may extend from near the hook panel 106 a length 109 of several inches. The length 109 may extend the entire length 33A, 43A, 53A, 63A, 73A of a strap 12, 14, 16, 18, 20, respectively. The exact lengths 107, 109 of the hook panel 106 and loop panel 108, respectively, may be selected to promote sufficient engagement of the hook panel 106 and loop panel 108 to support forces applied by a seated person against the restraint 10. The hook panel 106 and loop panel 108 may be reversed in any or all of position, size, or surfaces 102, 104.

Figure 8:
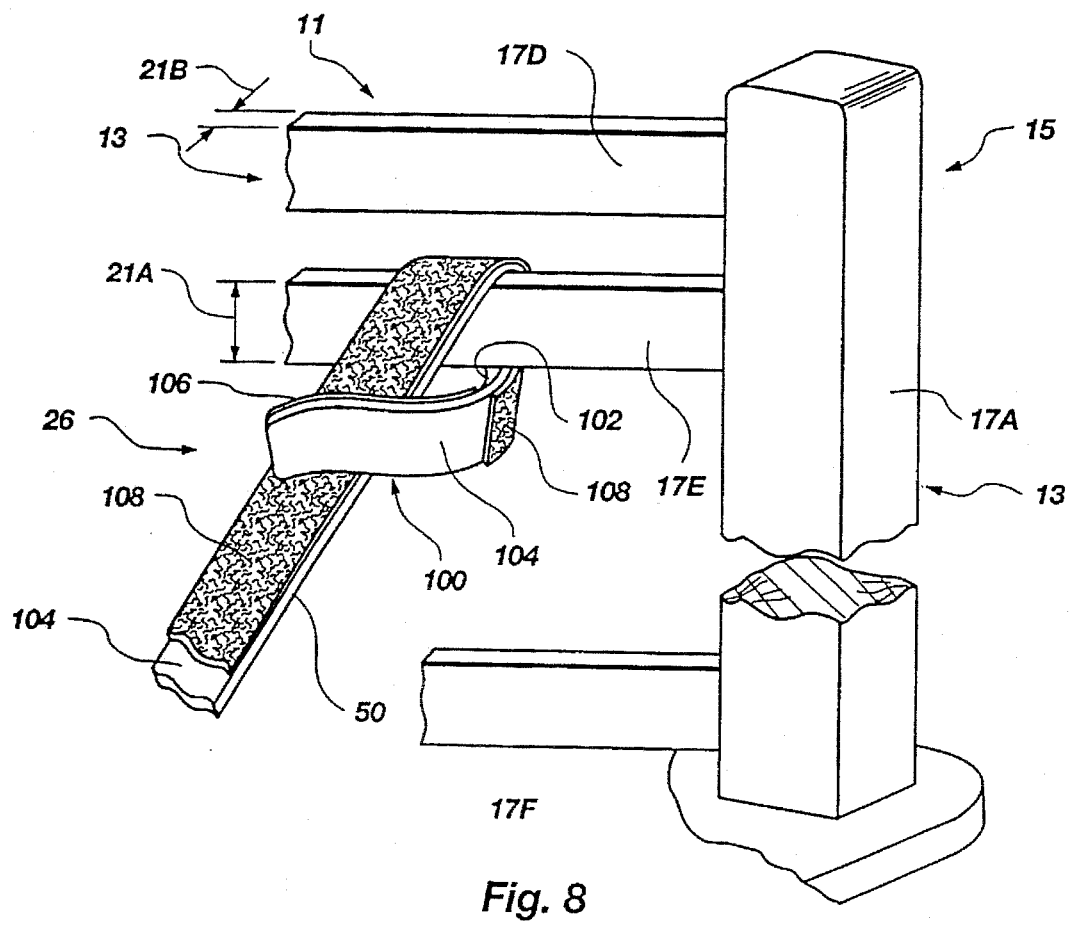

In an alternative embodiment of FIG. 8, the hook panel 106 may be on one surface, 102, 104, while the loop panel may be on the other surface 104, 102 of the tongue 100 of any strap 12, 14, 16, 18, 20. In this embodiment, the tongue 100 may be wrapped around a member 13 of the seatback 11 one or more times to provide more secure attachment to the member 13.

The fasteners 26 may each be opened and closed by an operator using the fingers of a single hand. Thus, although buckles, knots, hooks, snaps, and their equivalents are contemplated as fasteners 26, the illustrated, single-handed fasteners 26 may be easier to operate. Moreover, although any strap 12, 14, 16, 18, 20 could attach to any other, such an embodiment would require two hands to secure every fastener 26.

Alternatively, one may attach each strap 12, 14, 16, 18, 20 directly to the seatback 11. Such an embodiment reduces the length 33A, 43A, 53A, 63A, 73A of each respective strap 12, 14, 16, 18, 20 by almost half. Also, a user is restricted from shifting to a dangerous position with respect to the seat 17C or seatback 11. The result is simpler attachment to the seatback 11 and lighter weight, as well as smaller volume. A user is more secure in this arrangement. These benefits enhance cost, simplicity and portability of the restraint 10.

OPERATION

In operation the restraint 10 may be laid on a seat 17C of a chair 15. The lap strap 20 may be fastened by wrapping the associated tongue 100 around the nearest member 13. A child may then be set on the seat 17C and restrained with one hand. Each shoulder strap 16, 18 may be lifted over the appropriate shoulder of the seated person and attached as described above to the nearest member 13 of the seatback 11. The fasteners 26 at the ends 32, 34 of the waist strap 12 may then be secured, each to a nearest member 13 of the seatback 11.

The tongue 100 associated with each fastener 26 may be wrapped around the smaller aspect (width 21A or thickness 21B) of an associated elongate member 13 of the seatback 11. The tongue 100 may be wrapped more than once. The hook panel 106 of the fastener 26 may be then pressed to the loop panel 108 of the fastener 26 at a convenient position, securing the hook panel 106 to the loop panel 108.

The fasteners 26 at the ends 42, 44 of the optional chest strap 14 (if present) may then be similarly secured, in turn, each to its closest member 13 of the seatback 11. The adjusters 24, which may be attached to any or every strap 12, 14, 16, 18, 20, may then be pulled thereafter, or therebefore, to adjust the effective lengths 33A, 43A, 53A, 63A, 73A, respectively.

The restraint 10 may be quickly removed and replaced for the same child or other person without further adjustment. The restraint 10 may be removed and washed by any suitable means without damage, and without requiring any disassembly. The restraint can be folded or rolled up for carrying in a purse or diaper bag. The materials contemplated for construction of a basic restraint 10 with a minimum of adjusters 24 may weigh as little as several ounces.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An apparatus for use by an operator to restrain a user seated on a seat associated with a seatback, the apparatus comprising:

a first strap extending from a first end attached to a first location on a seatback to a second end attached to a second location on the seatback;

a second strap having a third end, the second strap being attached to extend from the first strap over a shoulder of the user to the third end attached to a third location on the seatback for urging the user toward the seatback;

a third strap having a fourth end, the third strap being attached to extend from the first strap over another shoulder of the user to the fourth end attached to a fourth location on the seatback for urging the user toward the seatback;

a fourth strap attached substantially transversely across the second and third straps proximate and below the arms of a user to extend from a fifth end adapted to be attached to the seatback to a sixth end adapted to be attached to the seatback away from the fifth end.

2. The apparatus of claim 1 further comprising a fifth strap having a seventh end, the fifth strap being attached to extend from a position on the first strap proximate the waist of a user, downwardly and between the legs of the user to attach to the seatback.

3. The apparatus of claim 1 further comprising:

a first fastener attached to the first end for attaching the first end to a first member of the seatback;

a second fastener attached to the second end for attaching the second end to a second member of the seatback; and the first and second fasteners comprising connectors operable to be secured to the seatback by a single hand of an operator.

4. The apparatus of claim 3 further comprising:

a third fastener connected to the third end to be attachable to a third member of the seatback; and a fourth fastener connected to the fourth end to be attachable to a fourth member of the seatback; and the third and fourth fasteners comprising connectors operable to be secured to the seatback by a single hand of an operator.

5. The apparatus of claim 1 wherein the seatback comprises a plurality of elongate members, the apparatus further comprising a fastener attached to the first strap and having a hook panel securable to a member of the plurality of elongate members by a loop panel.

6. The apparatus of claim 1 wherein the first strap, second strap, and third strap are comprised of a material selected to be substantially inextensible in a lengthwise direction and flexible in a transverse direction.

7. An apparatus for use by an operator to restrain a user seated on a seat associated with a seatback, the apparatus comprising:

a first strap extending from a first end attachable to a first location on a seatback to a second end attachable to a second location on the seatback;

a second strap having a third end, the second strap being attached to extend from the first strap over a shoulder of the user to the third end attachable to a third location on the seatback;

a third strap having a fourth end, the third strap being attached to extend from the first strap over another shoulder of the user to the fourth end attachable to a fourth location on the seatback; and an adjuster adapted to adjust a length of a strap selected from the first strap, second strap, and third strap.

8. The apparatus of claim 7 wherein the adjuster further comprises a control for selectively taking up and releasing the strap, the control being operable by a single hand of an operator.

9. The apparatus of claim 7 wherein the strap is formed to have a first portion and a second portion, the second portion being separated from the first portion, the adjuster being positioned therebetween and further comprising:

a first loop attached to the first portion;

an adjustable connector secured to the first loop; and a second loop attached to the second portion and threaded through the adjustable connector, the adjustable connector being selectively positionable along a length of the second loop.

10. An apparatus for restraining a user to a seatback of a chair, the chair having a plurality of members, each member of the plurality of members having an elongate aspect and a lesser aspect, the apparatus comprising:

a plurality of straps cooperatively interconnected to extend across the body of a user;

a plurality of fasteners, wherein a fastener of the plurality of fasteners is operatively and correspondingly associated with a strap of the plurality of straps to selectively secure the strap to a member of the plurality of members, the member corresponding to the strap; and a first and second strap of the plurality of straps extending over the shoulders of a user for urging the user toward the seatback, each of said first and second straps having a free end, and each of said free ends having secured thereto fastening means adaptable to be secured directly to the seatback.

11. The apparatus of claim 10 wherein the fastener comprises a clip securable to the member of the seatback.

12. The apparatus of claim 10 wherein the fastener further comprises an elongate portion adapted to extend around the lesser aspect of the member.

13. The apparatus of claim 12 further comprising at least one adjuster attached to the strap for adjusting a length of the strap.

14. The apparatus of claim 13 wherein each strap of the plurality of straps has attached thereto an adjuster of the at least one adjuster.

15. The apparatus of claim 13 wherein the adjuster is the fastener.

16. The apparatus of claim 10 wherein each strap of the plurality of straps has secured thereto a fastener of the plurality of fasteners; said fastener being operable to be secured to the seatback by a single hand of a user.

17. An apparatus for restraining a user to a seatback of a chair, the chair having a plurality of members, each member of the plurality of members having an elongate aspect and a lesser aspect, the apparatus comprising:

a plurality of straps cooperatively interconnected to extend across the body of a user;

a plurality of fasteners, wherein a fastener of the plurality of fasteners is operatively and correspondingly associated with a strap of the plurality of straps to selectively secure the strap to a member of the plurality of members, the member corresponding to the strap; and the strap formed to have a first portion, and a second portion separated from the first portion, an adjuster being positioned therebetween and further comprising:

a first loop attached to the first portion;

an adjustable connector secured to the first loop; and a second loop attached to the second portion and threaded through the adjustable connector, the adjustable connector being selectively positionable along a length of the second loop.

18. An apparatus for restraining to a front side of a seatback a person seated on a seat associated with the seatback, the person having arms, shoulders, legs, a waist, and a chest, the restraint comprising:

a waist strap having a first end and a second end for extending across the front of the waist of the person, the waist strap including a first end and a second end, the first end and the second end extending to the seatback;

a chest strap spaced upwardly away from the waist strap for extending across the front of the chest and under the arms of the person, the chest strap including a left end and a right end, the left end and the right end extending to the seatback;

a left shoulder strap connected to the waist strap and the chest strap to extend over one shoulder of the person to terminate at a first free end;

a right shoulder strap connected to the waist strap and the chest strap to extend over another shoulder of the person to terminate at a second free end;

a first fastener attached to the first end for fastening the first end to the seatback;

a second fastener attached to the second end for fastening the second end to the seatback;

a left fastener attached to the left end for fastening the left end to the seatback;

a right fastener attached to the right end for fastening the right end to the seatback;

a third fastener attached to the first free end for fastening the first free end to the seatback; and a fourth fastener attached to the second free end for fastening the second free end to the seatback.

19. The apparatus of claim 18 further comprising at least one adjuster attached to selectively adjust a length of a strap selected from the waist strap, chest strap, left shoulder strap, and right shoulder strap.

20. The apparatus of claim 18 further comprising a lap strap attached to the waist strap for extending between the legs of the person, the waist strap having a seventh end, and a fastener being attached approximate the seventh end for fastening the seventh end to the seatback.

* * * * *